United States Patent
D'Amelio

(10) Patent No.: US 11,836,922 B2
(45) Date of Patent: Dec. 5, 2023

(54) SYSTEM AND METHOD FOR EVALUATING EFFECTIVENESS OF A SKIN TREATMENT

(71) Applicant: Zerigo Health, Inc., San Diego, CA (US)

(72) Inventor: Frank D'Amelio, San Clemente, CA (US)

(73) Assignee: ZERIGO HEALTH, INC., San Diego, CA (US)

( * ) Notice: Subject to any disclaimer, the term of this patent is extended or adjusted under 35 U.S.C. 154(b) by 339 days.

(21) Appl. No.: 17/325,203

(22) Filed: May 19, 2021

(65) Prior Publication Data

US 2022/0383496 A1 Dec. 1, 2022

(51) Int. Cl.
*G06T 7/00* (2017.01)
*G06T 7/90* (2017.01)
(Continued)

(52) U.S. Cl.
CPC ........... *G06T 7/0016* (2013.01); *A61M 31/00* (2013.01); *A61M 35/00* (2013.01); *A61N 5/0616* (2013.01); *G06T 7/60* (2013.01); *G06T 7/90* (2017.01); *A61N 2005/0628* (2013.01); *A61N 2005/0661* (2013.01); *G06T 2207/10016* (2013.01); *G06T 2207/10024* (2013.01); *G06T 2207/20212* (2013.01); *G06T 2207/30088* (2013.01); *G06T 2207/30168* (2013.01)

(58) Field of Classification Search
CPC ........... G06T 7/0016; G06T 7/60; G06T 7/90; G06T 2207/10016; G06T 2207/10024; G06T 2207/20212; G06T 2207/30088; G06T 2207/30168; G06T 2207/30204; A61M 31/00; A61M 35/00; A61N 5/0616; A61N 2005/0628; A61N 2005/0661; A61N 2005/0627

See application file for complete search history.

(56) References Cited

U.S. PATENT DOCUMENTS

| | | | |
|---|---|---|---|
| 8,150,501 | B2 | 4/2012 | Stamatas |
| 10,130,297 | B2 | 11/2018 | Schnidar et al. |
| 2004/0008523 | A1 | 1/2004 | Butler |
| 2005/0119551 | A1 | 6/2005 | Maschke |
| 2006/0251408 | A1 | 11/2006 | Konno et al. |

(Continued)

FOREIGN PATENT DOCUMENTS

KR 2003-0083623 A 10/2003
WO WO-2012063467 A1 * 5/2012 ............. G06T 7/248

OTHER PUBLICATIONS

International Search Report and Written Opinion from PCT/US2021/070915, dated Oct. 7, 2021, 24 pages.
(Continued)

*Primary Examiner* — Mekonen T Bekele
(74) *Attorney, Agent, or Firm* — STEPTOE & JOHNSON LLP; Carl B. Wischhusen

(57) ABSTRACT

A method for evaluating the effectiveness of a skin treatment on a skin feature includes correcting the color of a first image before the skin treatment, correcting the color of a second image after the skin treatment, determining the sizes of the skin feature in the first and second images, and comparing the corrected colors and sizes of the skin feature in the first and second images. In some embodiments, the first and second images include the skin feature and an indicator adjacent to the skin feature, where the indicator has a standard color and a known size.

16 Claims, 8 Drawing Sheets

(51) Int. Cl.
  *G06T 7/60* (2017.01)
  *A61M 31/00* (2006.01)
  *A61M 35/00* (2006.01)
  *A61N 5/06* (2006.01)

(56) References Cited

U.S. PATENT DOCUMENTS

| | | |
|---|---|---|
| 2008/0051773 A1 | 2/2008 | Ivanov et al. |
| 2009/0143842 A1 | 6/2009 | Cumbie et al. |
| 2010/0214421 A1 | 8/2010 | Qu et al. |
| 2013/0289416 A1 | 10/2013 | Feferberg |
| 2015/0099947 A1* | 4/2015 | Qu ................ A61B 5/442 600/306 |
| 2016/0174878 A1 | 6/2016 | Grove et al. |
| 2017/0196795 A1 | 7/2017 | Takozaki et al. |
| 2017/0236281 A1 | 8/2017 | DaCosta |
| 2017/0246473 A1 | 8/2017 | Marinkovich et al. |
| 2018/0117355 A1 | 5/2018 | Loupis et al. |
| 2019/0000379 A1 | 1/2019 | Kokolis |
| 2020/0113438 A1 | 4/2020 | Parulian et al. |
| 2020/0121944 A1 | 4/2020 | Strahan et al. |
| 2020/0193580 A1 | 6/2020 | McCall et al. |
| 2020/0398075 A1 | 12/2020 | Pfiffner et al. |
| 2021/0001141 A1 | 1/2021 | Pfiffner et al. |

OTHER PUBLICATIONS

International Search Report and Written Opinion from PCT/US2022/081049, dated Mar. 22, 2023, 18 pages.
International Search Report and Written Opinion from PCT/US2022/081050, dated Mar. 23, 2023, 15 pages.
Aydin et al., "A practical method for the estimation of vitiligo surface area: a comparison between the point counting and digital planimetry techniques," European Journal of Dermatology, vol. 17, No. 1, Jan.-Feb. 2007, pp. 30-32.
Hayashi et al., "A novel three dimensional imaging method for the measurement of area in vitiligo and chemical leukoderma," Journal of Dermatological Science (Letters to the Editor), 84, 2016, pp. 219-221.
Kohli et al., "Three-dimensional imaging of vitiligo," Experimental Dermatology, 2015, 24, pp. 879-880.
Mythili et al., "Design and Development of an Area Estimating System to Find the Body Surface Area Affected by Vitiligo Using Simulation Approach," International Journal of Advanced Research in Computer Science and Software Engineering, vol. 2, Issue 3, Mar. 2012, pp. 75-81.
Oh et al., "Quantitative method for measuring therapeutic efficacy of the 308 nm excimer laser for vitiligo," Skin Research and Technology 2012, 18, pp. 347-355.
Partl et al., "128 Shades of Red: Objective Remote Assessment of Radiation Dermatitis by Augmented Digital Skin Imaging," Health Informatics Meets eHealth, 2017, pp. 363-374.
Partl et al., "Testing the feasibility of augmented digital skin imaging to objectively compare the efficacy of topical treatments for radiodermatitis," PLoS ONE, 14(6), Jun. 10, 2019, pp. 1-11.
Sheth et al., "A pilot study to determine vitiligo target size using a computer-based image analysis program," Journal of the American Academy of Dermatology, vol. 73, No. 2, Aug. 2015, pp. 342-345.

* cited by examiner

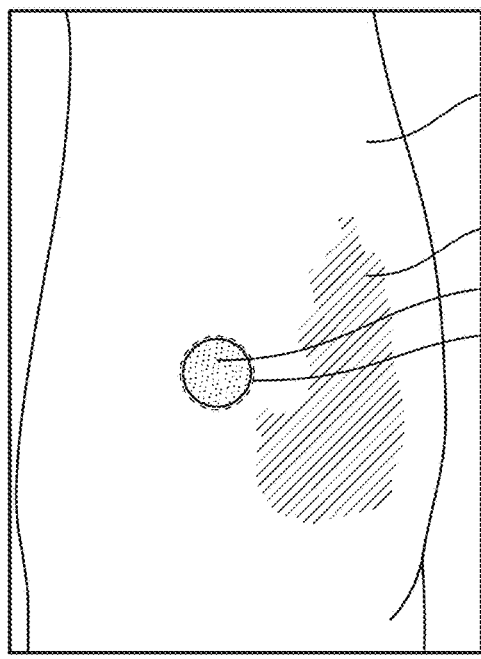 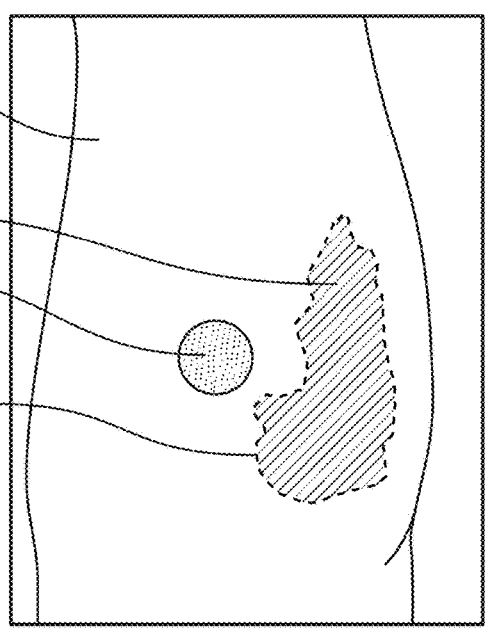
FIG. 3A FIG. 3B
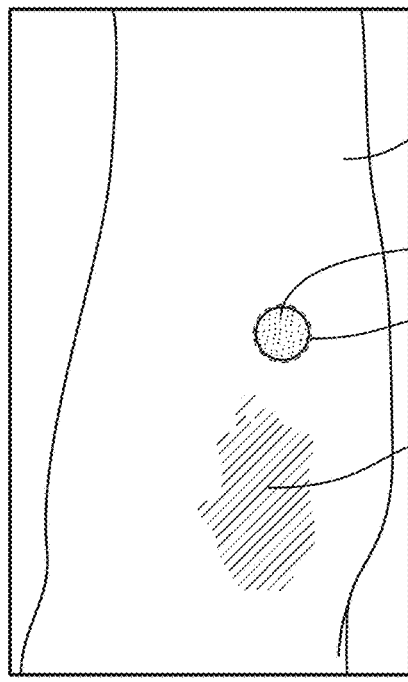 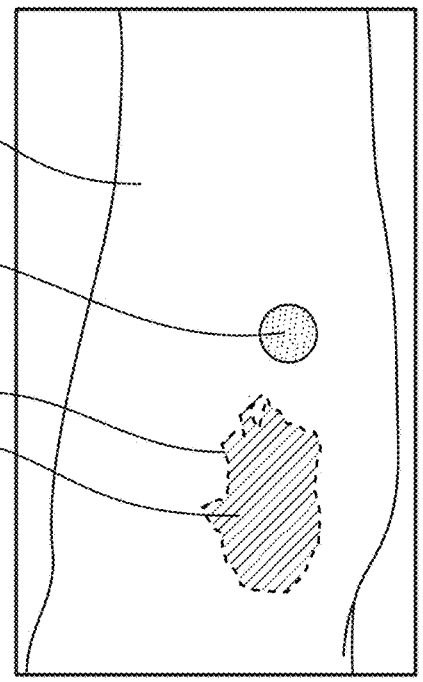
FIG. 4A FIG. 4B

SYSTEM AND METHOD FOR EVALUATING EFFECTIVENESS OF A SKIN TREATMENT

BACKGROUND

One set of ailments afflicting people are skin lesions. Patients who are being treated for skin lesions as well as their healthcare providers (and maybe even insurance companies) often want to know if the treatment is working. A treatment often does not effect immediate relief, so it is difficult to evaluate over the course of time whether the lesions are decreasing in size and/or severity. Patients and/or healthcare providers often take "before" and "after" (sometimes referred to as "comparison") images of the lesions to determine the size or surface area before and during (the "after" images) treatment. Typically, these comparison images suffer from differing distances and/or magnifications, differing lighting and/or color temperatures, poor focus, and differing image angles.

BRIEF DESCRIPTION OF THE DRAWINGS

FIGS. 3A-3B are examples of "before" images, according to embodiments of the present invention;

FIGS. 4A-4B are examples of "after" images, according to embodiments of the present invention;

Figure 1A:
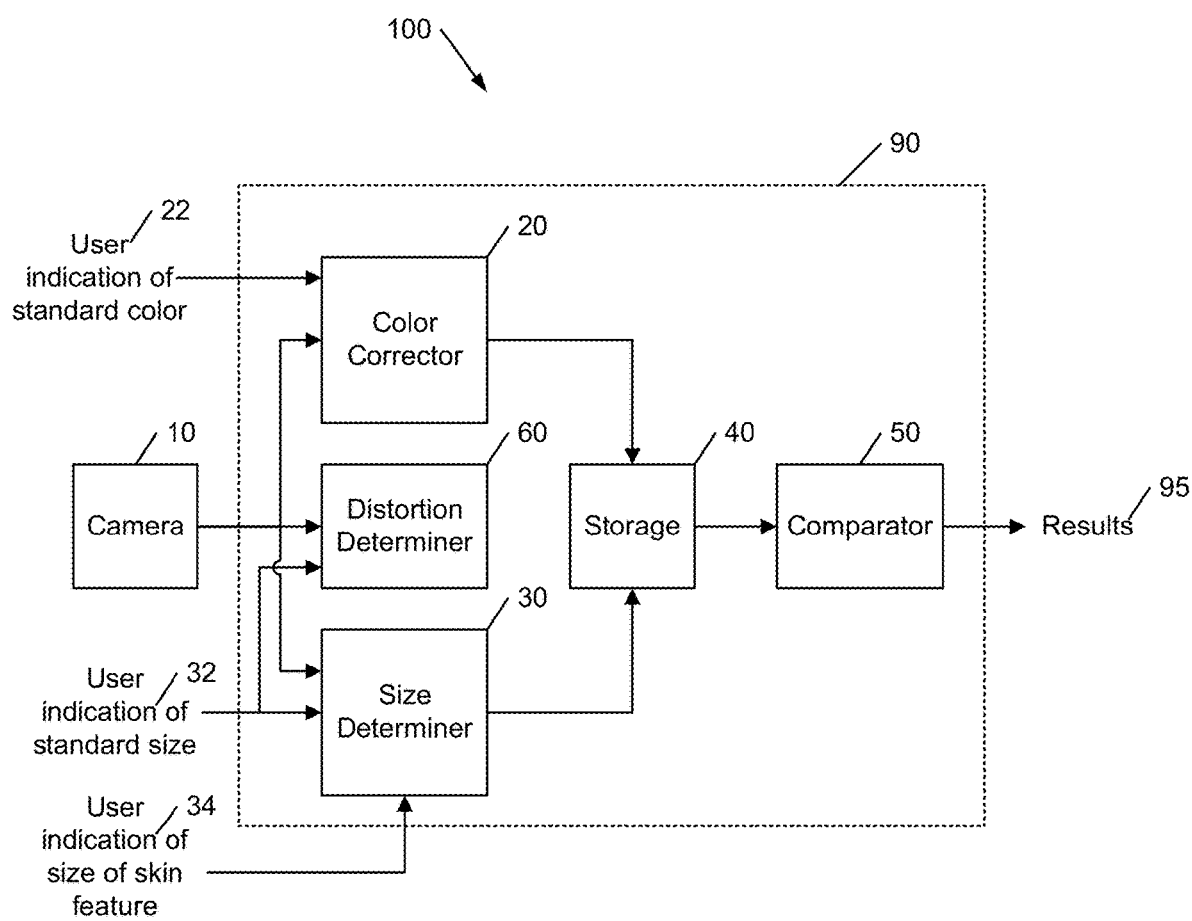
FIG. 1A is a block diagram of a system for evaluating the effectiveness of a skin treatment, according to an embodiment of the present invention.

Where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of embodiments of the invention. However, it will be understood by those of ordinary skill in the art that the embodiments of the present invention may be practiced without these specific details. In other instances, well-known methods, procedures, components, and circuits have not been described in detail so as not to obscure the present invention.

The problems mentioned above can mask the effectiveness of a skin treatment. For example, the "before" image may be taken at a certain distance from the lesion, at certain compound angles (i.e., not normal to the lesion), and at a certain magnification. If the "after" image is taken at a closer distance, at less normal an angle, or at a greater magnification (or some other combination of distance, angle, and magnification), the skin lesion may appear to have grown, even if that is not actually the case. Similarly, if the "after" image is taken at a further distance, at more normal an angle, or at a lesser magnification (or some other combination of distance, angle, and magnification), the skin lesion may appear to have shrunk, or shrunk to a greater degree than had actually occurred.

The color of the skin lesion and the surrounding tissue may also be evaluated to determine the effectiveness of a skin treatment. But the color, hue, tint, cast, temperature, and bias of an image may be influenced by external elements other than the true color of the skin and skin lesion. These external elements, which may include whether the image is taken with or without a flash, under fluorescent or incandescent or natural lighting, indoors or outside, or under bright sunlight or clouds, all considered to be external illumination, can all impact the perceived color of a before or after image. Thus, skin lesion diagnosis based on color may be inaccurate and possibly dangerous (if, for example, the patient's skin is getting redder because the treatment is too strong, the color and/or external illumination may mask the true redness of the treated tissue).

Another imaging challenge is contrast, which is the difference between dark and light. Poor lighting on an object may make it difficult to discern details, resulting in poor image contrast.

Another imaging challenge is focus. A skin lesion should be imaged in sharp focus for optimal evaluation. But a simple camera, such as one incorporated into a smartphone or a cellphone, or having an inexperienced photographer, such as a patient, may result in focusing on an object other than the skin lesion (such as an object in the background or foreground).

Another imaging challenge is motion blur. A patient who is imaging his or her own skin may easily move the body part at issue and/or may move the camera or cellphone itself (or at least not hold it steady), especially when imaging a body part that is difficult to access, such as a neck, back, or buttocks.

Another related problem is the accurate determination of Minimal Erythema Dose (MED), which is the effective starting treatment dose for skin therapy. The MED is the point at which the treatment begins to elicit a skin reaction such as some redness (called "erythema"). For example, patients having different skin types can tolerate different levels of treatment. If the treatment uses ultraviolet (UV) radiation, a patient may be told to begin at a low energy level, e.g., 200 mJ/cm$^2$, to determine whether such treatment has any effect on the skin. If there is no reaction, the patient increases the dosage by some amount, e.g., to 250 mJ/cm$^2$, and again looks for a skin reaction. The dosage may be increased up to, for example, 1000 mJ/cm$^2$, in 50-100 mJ/cm$^2$ increments. Patients and/or healthcare providers may take before and after images to determine whether the skin gets redder as a consequence of this increasing dosage regimen. But the problems identified above make the accurate detection of skin redness difficult, and thus MED is often difficult to determine.

If one wants an accurate assessment of lesion shrinkage progress or an accurate determination of the MED, one needs to evaluate the treated lesion at the same magnification, which requires that the camera be held at exactly the same distance and angle each and every time an image is taken. Often the period between the taking of images after treatments is weeks or months. Thus, keeping the magnification constant is nearly impossible. Even if the before and after images are taken with the same camera, the problems of differing distances and/or magnifications, differing lighting conditions and/or color temperatures, poor contrast, poor focus, motion blur, and differing image angles still exist.

One way of addressing some of these problems is to affix a conical adapter to the cellphone that fits between the lens of the cellphone camera and the skin lesion. This minimizes changes in distance between the camera and the skin lesion, but the conical adapter limits the field of view of the camera (and thus the size of the lesion visualized), and there still may be distortion in one or more of the images if the conical adapter is not seated flush against the skin in the same way every time.

The inventor has developed a system and method to evaluate the effectiveness of a skin treatment by addressing these challenges. The method involves affixing an indicator adjacent to a skin feature, such as a skin lesion that is being treated using a therapy, such as light, radiation, thermal, or medicinal therapy (e.g., drugs, creams, etc.). The indicator and the skin feature are imaged together so as to generate a first image, which is the before image. The indicator has a known, standard color or tone (e.g., black/white/gray) so that the color of the first image influenced by external illumination can be corrected (or the color cast can be removed). The indicator (and all subsequent indicators used) has a known size so that the size of the skin feature can be determined (or at least the relative sizes of the skin feature in the before and after images). The first image along with its corrected color and size information may then be stored. At a later time, the indicator and the skin feature are imaged together so as to generate a second image, which is the after image. (There may be multiple "after" images made at different times.) The color of the second image can be corrected, and the size of the skin feature in the second image can be determined (or at least the relative sizes of the skin feature in the before and after images). As corrected, the color and size of the skin feature in the second image can then be compared to the color and size of the skin feature in the first image to determine if there has been improvement in the condition of the skin feature.

As used herein, a "first image," "first picture," "first photograph," "before image," or "before picture" indicates an image that is taken before a "second image," "second picture," "second photograph," "after image," or "after picture." A comparison is made between an earlier image and a later image.

In one embodiment, a patient may take a photograph of their skin feature with a camera or cellphone periodically during treatment. The patient may upload the photographs to a remote storage location for analysis.

Reference is now made to FIG. 1A, which is a block diagram of a system 100 for evaluating the effectiveness of a skin treatment, according to an embodiment of the present invention. System 100 includes camera 10 connected to application 90, which includes color corrector 20, size determiner 30, storage 40, comparator 50, and distortion determiner 60. Camera 10 is preferably any type of digital camera, although an analog camera may be used with some modifications (e.g., digitizing an analog image). The output of camera 10 is the digital information regarding the intensity and color of each pixel in an image.

Figure 1B:
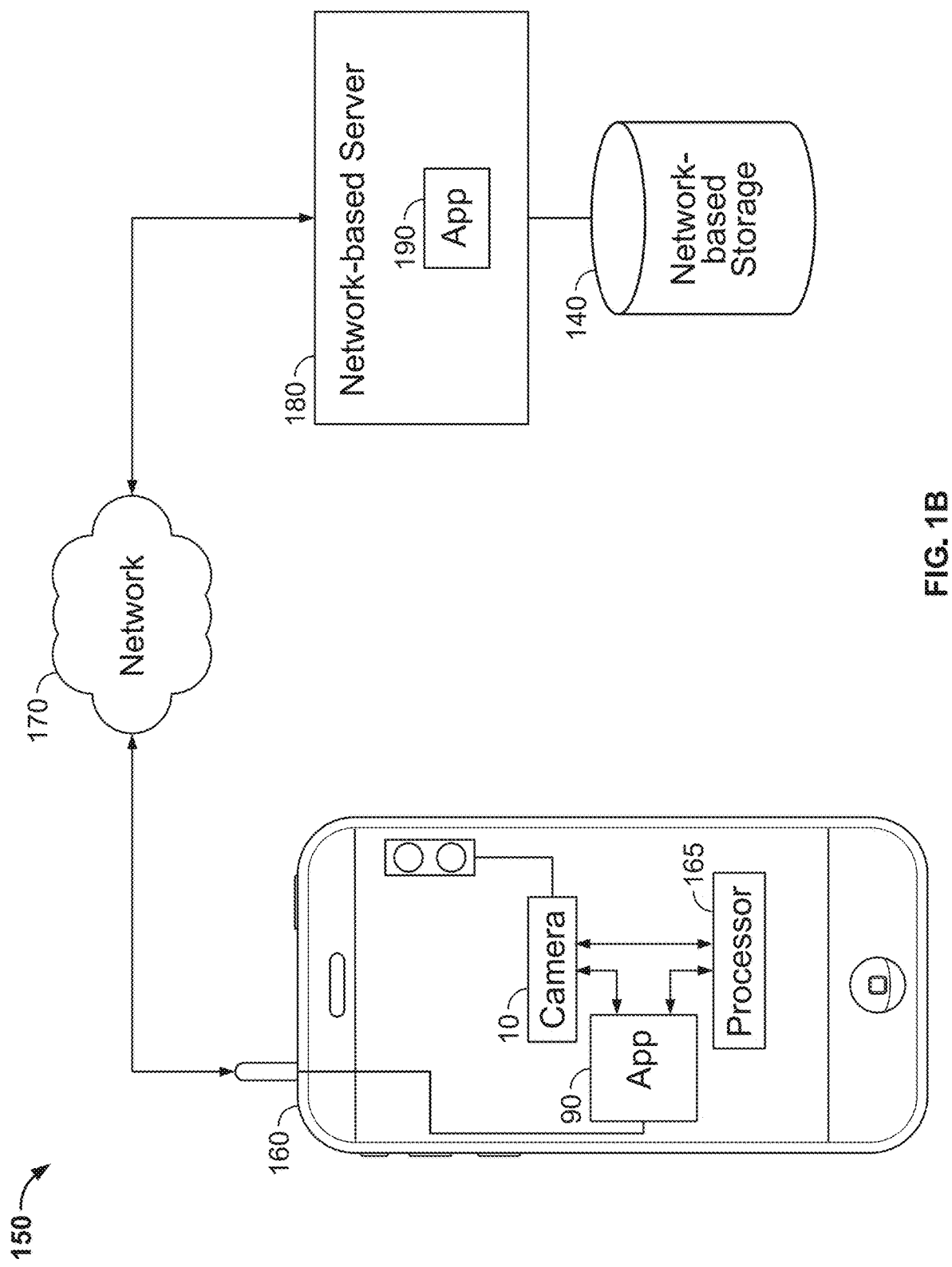
FIG. 1B is a block diagram of a broader network-based system that includes the system of FIG. 1A, according to an embodiment of the present invention.

System 100 may be part of a broader network-based system 150 shown in FIG. 1B. System 150 includes smartphone 160, within which is camera 10, application 90, and processor 165. Application 90 can communicate via network 170 to a network-based server 180, which may include a companion application 190. Application 190 may perform some of the computing functions that application 90 performs. Network-based storage 140 is connected to network-based server 180.

Figure 1C:
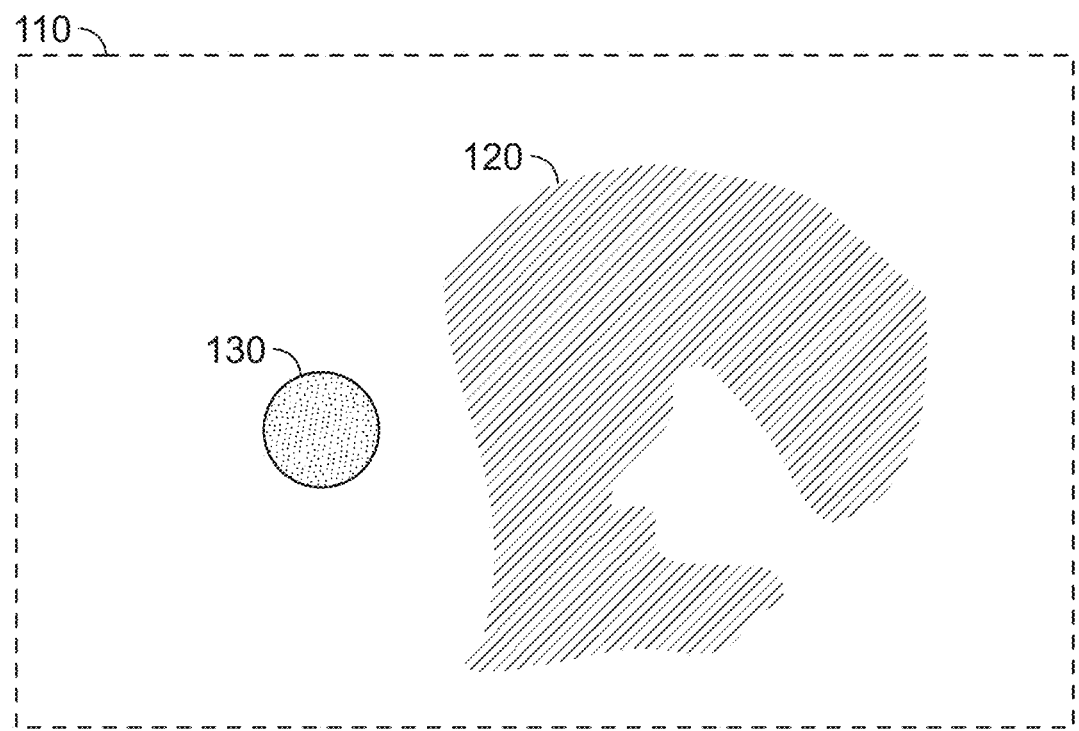
FIG. 1C is a schematic diagram showing a skin feature and an indicator used to correct the color and determine the size of a skin lesion (or other skin feature), according to an embodiment of the present invention.

In this invention, each image 110 includes a skin feature 120 and a colored indicator 130, as shown schematically in FIG. 1C. Skin feature 120 may be any type of skin lesion, such as may occur in acute and chronic skin conditions such as psoriasis, vitiligo, eczema, and rosacea, as well as moles, scars, sunburn, skin cancer, ecchymosis (bruising), hematomas (black and blue lesions), dark circles under the eyes (periorbital dark circles), and other conditions. Colored indicator 130 has a known size (dimension), shape, and color, and acts as a standard for measuring the size and color of the skin feature. Colored indicator 130 may be of any shape, but a regular shape (e.g., circle, square, rectangle, oval, triangle, polygon) is preferred. Colored indicator 130 may have any color or tone, including white, black, or gray, so long as the color can be known and standardized, for example its red, green, and blue components (RGB) may be specified and controlled. Other color conventions, for example, HSL (hue, saturation, lightness), HSV (hue, saturation, value), and CMYK (cyan, magenta, yellow black), may also be used. Colored indicator 130 may take the form of a "sticker," with a mild adhesive to aid in placement near the skin feature.

In operation, a user who is trying to determine the effectiveness of a skin treatment views image 110, identifies to system 100 the standard color to be used for color correction, and identifies to system 100 the size to be used as the standard for measurement, as well as the size of the skin feature. More specifically, in one embodiment, the user may use a tool such as a mouse and click on the color of colored indicator 130 to indicate to system 100 that that color is the standard color to use to correct the color of the image. The user then indicates to system 100 the RGB values or components of colored indicator 130. Next, with the mouse, the user may outline the shape of indicator 130 to indicate to system 100 that that size is the standard size to use for determining the size of the skin feature. Alternatively, with the mouse the user may click on indicator 130, and system 100 may be able to outline the shape of (i.e., edge detect) indicator 130 itself and use that shape as the standard size for determining the size of the skin feature. The user may then indicate to system 100 the exact size (e.g., surface area or dimensions) of indicator 130, if an absolute measurement of the size of skin feature 120 is desired. Finally, the user outlines the shape of skin feature 120.

As described above, camera 10 outputs digital information regarding the color and intensity of each pixel in an image such as image 110. Color corrector 20 takes as an input the output from camera 10 as well as input 22 from the user regarding the standard color to be used to correct the color of the skin feature. This user input may be a mouse click on indicator 130 along with information regarding the standard color (e.g., RGB value, HSL value, etc.). The standard color may be white (RGB=255,255,255), black (RGB=0,0,0), or gray (RGB=equal values of R, G, B), or any other RGB combination. The key is to use the same colored indicator 130 in both the before and after images and to inform color corrector 20 in both cases of indicator 130's color. Also, using standard color card colors (e.g., from the Standard Reference of America or the Standard Color Card of America, ColorChecker charts, IT8 charts) may be easier because they are more readily available. The inventor has found that using a gray color, such as a middle gray, may work better than white to correct the color of the skin feature. An example of a standard middle gray is Kodak's 18% reflectance card. The RGB value for this color is 127, 127, 127 (or, sometimes, 128, 128, 128).

Color corrector 20 may use or incorporate software code that allows a user to identify the color area to be used as the color standard. This software may be proprietary or commercial, publicly available software such as Adobe® Photoshop®, ImageJ (National Institutes of Health), or GIMP (GNU Image Manipulation Program). Such software adjusts the color of each pixel from camera 10 to correct it using the standard color the user inputs to color corrector 20. This adjustment removes the color cast and/or an amount of color from the images. The output of color corrector 20 can be a corrected image and/or the digital information of the corrected image—color information for each pixel of the corrected image. This information may then be stored in storage 40.

Figure 1D:
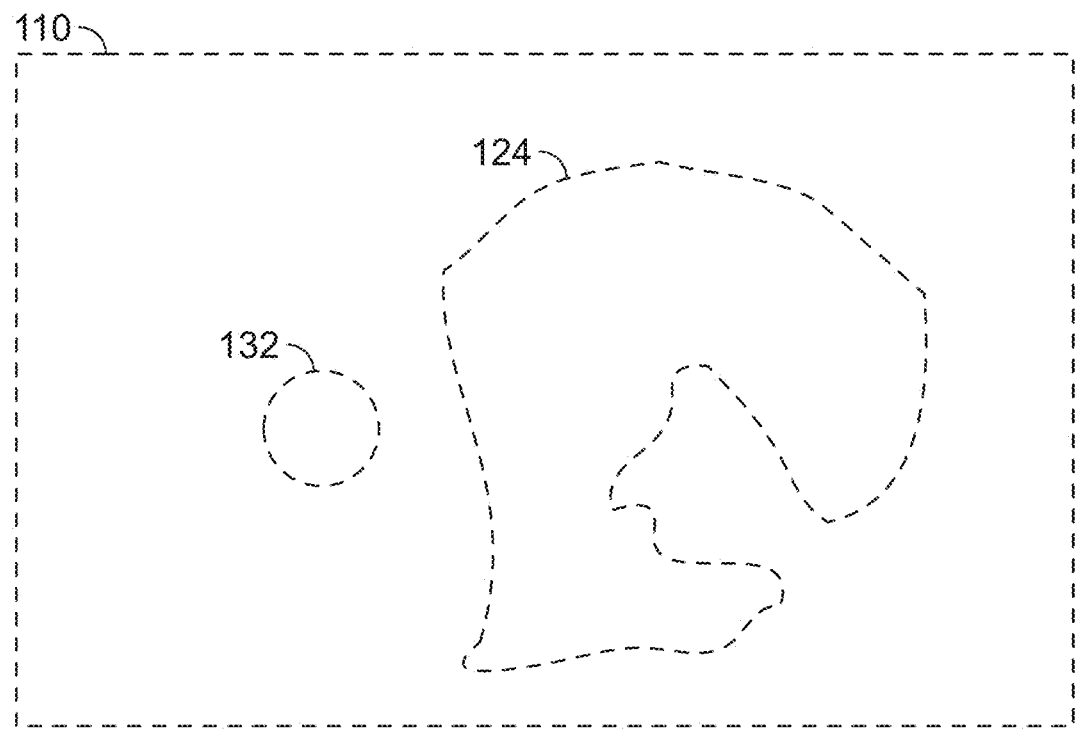
FIG. 1D is a schematic diagram showing outlines of the skin lesion (or other skin feature) and indicator from FIG. 1C, according to an embodiment of the present invention.

Similar to color corrector 20, size determiner 30 takes as an input the output from camera 10 as well as input 32 from the user regarding the standard size to be used. This user input may be an outlined area or perimeter indicated by the user, such as dotted area 132 shown in FIG. 1D. Alternatively, the software may be able to determine the edge or boundary of colored indicator 130 after the user clicks on the indicator in the image. For example, the software may use a 3-D intensity histogram to identify the area of colored indicator 130, by, e.g., identifying which pixels in an area exceed a certain intensity threshold. In an embodiment that allows the system to determine the actual size of the skin feature (as opposed to relative size in before and after images), the user may inform the system of the actual size of colored indicator 130 in inches or millimeters, such as by area or by dimensions, e.g., by radius or diameter (if a circle) or height and width (if a rectangle). There may also be a user input 34 to outline the area of the skin feature, such as dotted area 124 shown in FIG. 1C. As with color correction, the key in size determination is to use the same colored indicator 130 in both the before and after images and to indicate the same size to size determiner 30 in both cases.

Size determiner 30 may also use software to measure the relative or actual size of skin feature 120. With respect to relative size, the software may determine the number of pixels attributable to or within colored indicator 130 in the before and after images. This ratio $$\left( \frac{\text{\# pixels before}}{\text{\# pixels after}} \right)$$

is the magnification ratio of the two images. This ratio is then used to correct (i.e., scale up or down) the areas of the skin feature in the two images. For example, if the number of pixels in dotted area 132 in the before image is 100,000 and the number of pixels in dotted area 132 in the after image is 120,000, the ratio is 0.833. That ratio is then used to scale down the area of the skin feature in the second image, as will be described in more detail below.

With respect to actual size, the software may determine the area of the skin feature by comparing the number of pixels attributable to the indicator and the number of pixels attributable to the skin feature (i.e., using dotted areas 132 and 124). For example, if the number of pixels in dotted area 132 is 100,000 and the area of indicator 130 is 0.4 square inches (correlating to ~0.71 inch diameter—e.g., about the size of a U.S.A. dime), if the number of pixels in dotted area 124 is 1,300,000, then the area of skin feature 120 is 5.2 square inches (1,300,000 pixels/100,000 pixels×0.4 square inches). The output of size determiner 30 can be the digital size information (pixels, area) of the skin indicator 130 and skin feature 120. This information may then be stored in storage 40 along with image 110.

Storage 40 is typically any type of non-volatile storage, so that the information for a first image may be saved to be compared later to information for a second and subsequent images. Alternatively, if a user compares the before and after images at the same time, for example at or around the time the second image is taken, storage 40 may be volatile storage (e.g., RAM) that is used to store the information temporarily while the comparison is being performed. The storage may be on the camera or cellphone itself or may be on a memory card (e.g., SD or microSD card) or remote (e.g., on server 180, in the "cloud," or in a commercial portal or repository such as storage 140) and accessed via a wired or wireless network, such as network 170, or over the Internet.

Comparator 50 may be used to compare the color and size of different images of skin features. In operation, the user takes a second image 110, an after image. For skin features that are being treated by light therapy, such images may typically be taken monthly, but can be taken one or two weeks later or even months later. For other applications in which the feature being evaluated changes more rapidly, an after image may be taken hours or days later. Many after images may be taken for comparison. In addition, videos may be taken, and frames may be extracted from the videos as images. Moreover, multiple images may be taken of large skin features, and these multiple images may be stitched together in a panorama.

The second image is processed in the same way the first image was processed—using color corrector 20 and size determiner 30—with the user indicating to system 100 the color and size of colored indicator 130 and the outline or extent of skin feature 120. The same (or equivalent in size and color) colored indicator 130 must be used for both images. After system 100 determines the corrected color of each pixel in the second image, comparator 50 can compare the corrected color of each pixel in the first image and output the results 95. This output may be in the form of another image that shows the differences in color in a region of interest. The output may also show changes in a region of the images, such as the skin feature itself or an area of healthy skin. The output may also compare the colors of areas of the skin feature rather than the whole skin feature.

In one embodiment, the system may compare areas of the skin outside of a typical skin lesion. (In such instances, the area of the skin may be considered a type of "skin feature" as described above.) This may be helpful in identifying problems with the light or radiation therapy or when to decrease the light or radiation energy output setting. For example, one type of therapy may use UV radiation (e.g., UV-B radiation or narrowband UV-B radiation) to treat the skin feature. However, the user's skin may react to the application of too much energy and the skin feature may be overtreated or areas of the skin other than the skin feature may be treated, which may cause the skin to develop an erythema (skin redness) reaction, a burn reaction, or another skin condition. System 100 may be able to identify such erythemic portions of the skin by comparing the corrected color of that portion of the skin in the after image to the corrected color in the before image. System 100 may have stored within it skin colors that are indicative of erythema or other light therapy overtreatments, and may be able to warn the user regarding such erythema or skin condition. This may also allow the user to either stop increasing the device's energy or stopping treatment for a period of time. Thus, the invention may indicate to the user both improvements and deteriorations in skin condition.

Results 95 may also include increases or decreases in the size of skin feature 120. Reference is made again to the example used above in which the area of indicator 130 (i.e., dotted area 132) in the first image comprises 100,000 pixels and the area of skin feature 120 (i.e., dotted area 124) in the first image comprises 1,300,000 pixels. The second image may be taken from a different distance away from the skin as the first image and/or using a different magnification from that of the first image. In the second image, size determiner 30 determines that colored indicator 130 comprises 120,000 pixels. This means that the size measurements in the second image need to be adjusted by the magnification ratio of the two images as described above, which in this case is 0.833. Thus, if dotted area 124 in the second image comprises 1,400,000 pixels, that number must be adjusted by the 0.833 ratio before comparing the relative sizes of the skin features in the two images. In this case, 1,400,000*0.833=1,166,667 pixels. Thus, the area of the skin feature has been reduced from 1,300,000 pixels to 1,166,667 pixels, which is about 10%

$$\left(\frac{1,300,000 - 1,166,667}{1,300,000} = 0.1026 = 10.26\%\right).$$

If actual measurements of the skin features are desired, the system uses the known size of colored indicator 130, which in this example is 0.4 square inches, corresponding to 100,000 pixels (dotted area 132) in the first image. Since dotted area 124 in the first image comprises 1,300,000 pixels, the area of skin feature 120 in the first image is 5.2 square inches. In the second image, the same 0.4 square-inch colored indicator comprises 120,000 pixels, resulting in the magnification ratio of 0.833. Again, dotted area 124 in the second image comprises 1,400,000 pixels, which is adjusted to 1,166,667 pixels. Thus, the area of skin feature 120 has been reduced from 1,300,000 pixels to 1,166,667 pixels, corresponding to a reduction from 5.2 square inches to 4.67 square inches.

In another embodiment, the second image may be taken with a different camera. This may occur if the patient upgrades his or her cellphone to one having a better camera (i.e., more megapixels leading to higher resolution) or if the patient (or, in the case of a minor, the patient's guardian) just happens to use a different camera. In this case, the magnification ratio must be adjusted by the camera pixel ratio. For example, the original camera may have a 6-megapixel (MP) resolution, and the later camera may have a 42 MP resolution. This pixel ratio (7:1) needs to be accounted for. In the relative scenario, the second image, which again may be taken from a different distance away from the skin as the first image and/or using a different magnification from that of the first image, yields 840,000 pixels for colored indicator 130. This means that the new magnification ratio is $$\frac{100,000}{840,000} = 0.119,$$

which is the previous ratio (0.833) divided by 7. Thus, if dotted area 124 in the second image comprises 9,800,000 pixels, that number must be adjusted by the 0.119 ratio before comparing the relative sizes of the skin features in the two images. In this case, 9,800,000*0.119=1,166,667 pixels (as before). Thus, the area of the skin feature has been reduced from 1,300,000 pixels to 1,166,667 pixels or by 10.26%.

The absolute size of the skin feature can also be determined using the new magnification ratio. The area of skin feature 120 in the first image was determined to be 5.2 square inches. In the second image, the same 0.4 square-inch colored indicator comprises 840,000 pixels, resulting in the new magnification ratio of 0.119. Again, dotted area 124 in the second image comprises 9,800,000 pixels, which is adjusted to 1,166,667 pixels. Thus, the area of skin feature 120 has been reduced from 1,300,000 pixels to 1,166,667 pixels, corresponding to a reduction from 5.2 square inches to 4.67 square inches.

In another embodiment, distortion determiner 60 in system 100 may measure distortion of the image, to ensure that the images being compared have sufficient undistorted quality. One way to measure distortion is to measure the angle at which the colored indicator and skin feature are being imaged. Having the camera positioned directly over the colored indicator and skin feature provides different size measurements compared to if the camera were positioned at another angle (e.g., at a grazing angle). One way to measure this angle is to calculate circularity, and if, for example, circularity falls below a certain threshold, the system can prompt the user to retake the image.

Circularity can be calculated using colored indicator 130 by measuring its height and width. Circularity is calculated by $$\text{Circularity} = \frac{4\pi A}{\text{Perimeter}^2}$$

or by comparing the height to the width. For a perfect circle (or if height=width), this equation reduces to 1. Thus, an image taken directly above the colored indicator (normal to the horizontal plane) should have a circularity of 1. As the angle at which the image is taken departs from the vertical, the size of the skin feature gets distorted. The colored indicator then has an elliptical projection in the image, and the circularity of the indicator decreases. To protect against such distortion, we may put a lower bound on acceptable circularity of, for example, 0.75. Below that threshold, system 100 may indicate to the user to take another image at a better, i.e., more normal, angle.

Distortion determiner 60 may also determine distortion caused by poor focus or blur. This will be described below with respect to FIGS. 6A and 6B.

The blocks shown in FIGS. 1A and 1B are examples of modules that may comprise the various systems described and do not limit the blocks or modules that may be part of or connected to or associated with these modules. For example, user input 32 is shown as an input to size determiner 30 and distortion determiner 60, but if the input is outlining the colored indicator, such outlining can also be used in color corrector 20. Comparator 50 may take inputs directly from color corrector 20 or size determiner 30 instead of from storage 40. Moreover, while color corrector 20, size determiner 30, comparator 50, and distortion determiner 60 are shown as blocks separate from other blocks, they may be implemented in a general data processor, such as processor 165, that performs other functions. The functions may also be performed on network-based server 180 and/or in companion application 190. The blocks in this figure may be implemented in software or hardware or a combination of the two, and may include memory for storing software instructions. The software may be in the form of one or more software development kits (SDKs). An SDK is a program that may run within smartphone 160 or other device to perform specific functions. In the embodiments of the present invention, such functions may include color correction, size determination, circularity calculation, and distortion determination.

Figure 2:
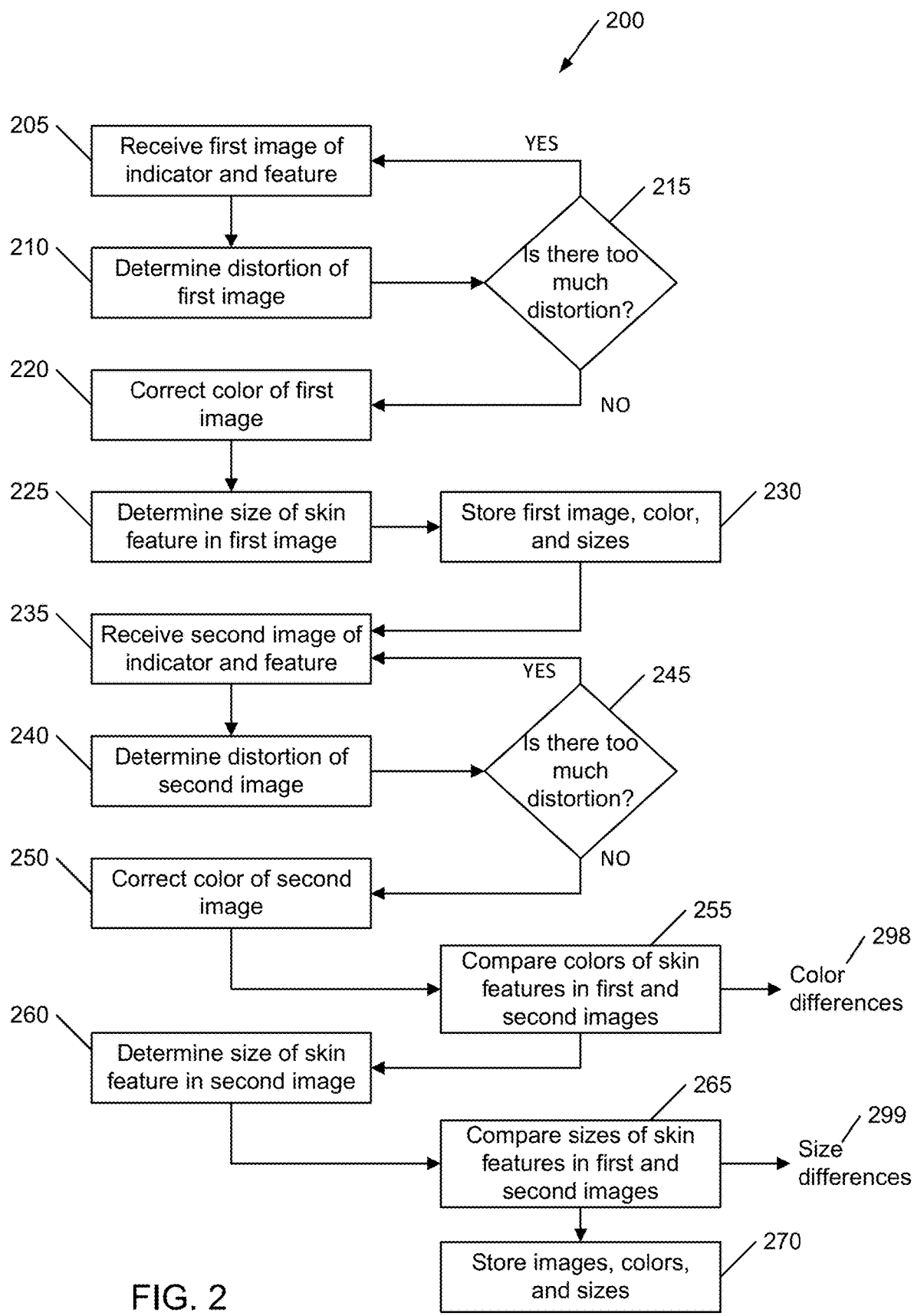
FIG. 2 is a flowchart showing a process for evaluating the effectiveness of a skin treatment, according to an embodiment of the present invention.

Reference is now made to FIG. 2, which is a flowchart showing a process 200 for evaluating the effectiveness of a skin treatment, according to an embodiment of the present invention. In operation 205, a first image 110 is received that includes colored indicator 130 and skin feature 120. This image may be taken by a user with camera 10. In operation 210, system 100 determines the distortion of the first image using distortion determiner 60. As discussed above, one measure of distortion may be determined by calculating the circularity of the first image. User input 32 includes indicating to system 100 the outline or extent of colored indicator 130 in image 110, for example by outlining indicator 130. In another embodiment, user input 32 may include touching (e.g., with a mouse or other pointer) just one part of colored indicator 130, and then distortion determiner 60 may be able to automatically determine the outline or extent of colored indicator 130. Once the outline or extent of colored indicator 130 is determined, distortion determiner 60 may calculate circularity using the previous equation. As described below with respect to FIGS. 6A and 6B, distortion determiner 60 may also determine if the image is not focused enough or is too blurry. Operation 215 determines whether there is too much distortion, for example if the circularity is less than a certain threshold, e.g., 0.75. If so, the distortion is not satisfactory and system 100 would direct the user to take the image again, and the process returns to operation 205. If there is not too much distortion, the image is considered satisfactory. Note that the distortion indication may occur in real-time or it may be delayed.

In operation 220, system 100 corrects the color of the first image using color corrector 20 and user input 22. From operation 210, the system knows (from user input 32) what color the colored indicator comprises in image 110. User input 22 may include indicating to system 100 the RGB values of colored indicator 130 if exact color correction of skin feature 120 is desired.

In operation 225, system 100 determines the size of the skin feature in the first image using size determiner 30 and user input 32. From operation 210, the system knows (from user input 32) what the outline or extent of colored indicator 130 comprises in image 110. User input 32 may also include indicating to system 100 the area or dimensions of colored indicator 130 if an exact size of skin feature 120 is desired. Size determiner 30 then determines the number of pixels skin feature 120 comprises and calculates its area if desired. Operation 230 stores in storage 40 image 110, the corrected color values of the pixels of image 110 and skin feature 120, and the number of pixels of colored indicator 130 and skin feature 120, as well as the sizes (i.e., areas) of both of these if known.

FIG. 2 also shows the operations to process the second image. Operations 235, 240, 245, and 250 are substantially the same as operations 205, 210, 215, and 220. Once the color of the second image is corrected in operation 250, the system may compare in operation 255 the corrected colors of the skin features in the first and second images using comparator 50. Comparator 50 may then output color differences 298 as described above—another image that shows the differences in color or an indication of the change in average colors of the skin features in the two images or a numerical indication for each pixel. Color differences 298 may also include a comparison of the colors of areas of the skin feature rather than the whole skin feature, as well as comparison of colors of skin outside of the skin feature, to warn of skin mistreatment, e.g., sunburn, by the therapy instrument. Color differences can be used for assessment of a subject.

Operation 260 is substantially the same as operation 225. Once the size of the skin feature in the second image is determined in operation 260, the system may compare the sizes of the skin features in the first and second images in operation 265 using comparator 50. Comparator 50 may then output size differences 299 as described above—increases or decreases in the size of skin feature 120, including listing the absolute sizes of the before and after skin features. In operation 270, the images, corrected colors, sizes (i.e., areas) of the colored indicator and the skin feature, and color and size differences are stored in storage 40, so that they may be used subsequently as "before" images for later images.

Besides the operations shown in FIG. 2, other operations or series of operations are contemplated to evaluate the effectiveness of a skin treatment. For example, although operations 205 and 235 indicate the receiving of images, these operations contemplate the acquisition of digital information from an image, so these operations may be accomplished or aided by scanning and digitizing a photograph or other image that had been previously taken. And although only two images are compared, the system may compare more than two images at a time, for example, to show progression or regression of the diseased condition.

Moreover, the actual order of the operations in the flowchart in FIG. 2 is not intended to be limiting, and the operations may be performed in any practical order. For example, color is determined before size as currently shown, but size may be determined before color or both may be determined simultaneously. Similarly, circularity does not need to be determined first, but may be determined before or after size and/or color are determined. In addition, the actual order of processing of the two images need not be performed as indicated in FIG. 2. That is, the image taken later in time (the after image) may be processed before the image taken earlier in time (the before image). The system just needs to understand which image is "before" and which image is "after."

Reference is now made to FIGS. 3A-3B and 4A-4B, which are embodiments of the present invention. FIGS. 3A-3B are examples of "before" images; FIGS. 4A-4B are examples of "after" images. FIG. 3A shows skin feature 320 on arm 310, colored indicator 330, and dotted area 332, indicating the outline of colored indicator 330. FIG. 3B is the same image showing skin feature 320 and colored indicator 330, but now shows dotted area 324, indicating the outline of skin feature 320. FIG. 4A is an after image, showing skin feature 320 on arm 310, colored indicator 330 in a different position, and dotted area 432, indicating the after outline of colored indicator 330. FIG. 4B is the same image as in FIG. 4A showing skin feature 320 and colored indicator 330, but now showing dotted area 424, indicating the after outline of skin feature 320.

The circularity of FIGS. 3A-4B and the change in the size of skin feature 320 were calculated. In FIGS. 3A-3B, the circularity was calculated by Adobe Photoshop to be 0.854, and in FIGS. 4A-4B, the circularity was calculated to be 0.806, so the distortion of the images was determined not to be excessive. (In certain software applications, the maximum circularity may not be 1.00. See, e.g., Yasuhiro Takashimizu & Maiko Iiyoshi, *New parameter of roundness R: circularity corrected by aspect ratio,* 3(2) Progress in Earth and Planetary Sci. (January 2016) (https://progearth-planetsci.springeropen.com/articles/10.1186/s40645-015-0078-x) (maximum circularity is 0.913 in ImageJ software).) In FIG. 3A, colored indicator 330 comprises 101,618 pixels as outlined in dotted area 332. In FIG. 3B, skin feature 320 comprises 647,018 pixels as outlined in dotted area 324. In FIG. 4A, colored indicator 330 comprises 91,775 pixels as outlined in dotted area 432. In FIG. 4B, skin feature 320 comprises 494,523 pixels as outlined in dotted area 424. The ratio of dotted area 332 to dotted area 432=101,618/91,775=1.1073. Thus, the size of dotted area 424 must be adjusted by a factor of 1.1073 before being compared to the size of dotted area 324. 494,523·1.1073=547,561. Thus, the size of skin feature 320 has been reduced by about 15.4%

$$\left(\frac{647,018 - 547,561}{647,018} = 0.1537 = 15.37\%\right).$$

Figure 5A:
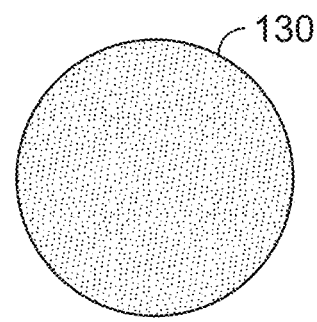
FIGS. 5A-5C are different examples of a size and color indicator, according to embodiments of the present invention.
Figure 5B:
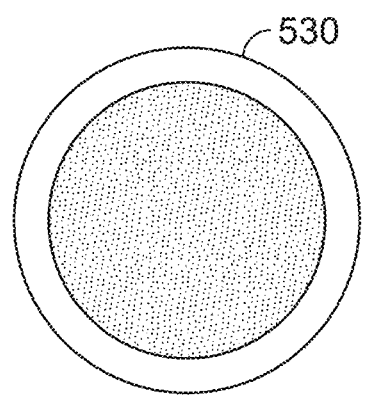
Figure 5C:
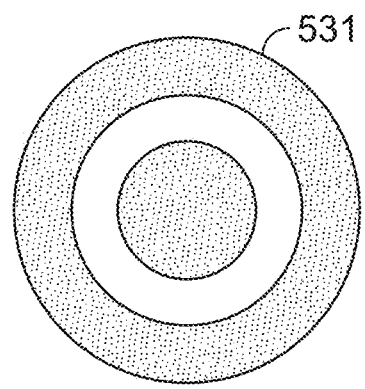

Reference is now made to FIGS. 5A-5C, which are different examples of a colored indicator, according to embodiments of the present invention. FIG. 5A shows colored indicator 130, which is the same as that shown in FIG. 1C. FIG. 5B shows colored indicator 530, which includes a white circumferential band around the previous color indicator. FIG. 5C shows colored indicator 531, which includes another gray band around the white band of the previous color indicator.

Figure 6B:
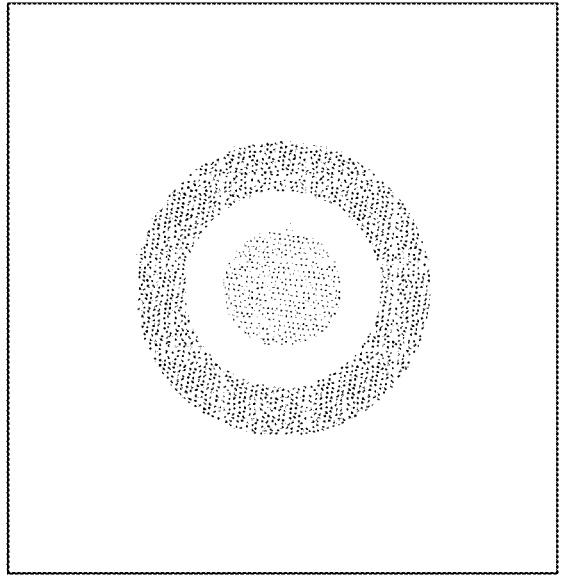
FIGS. 6A-6B show the effects of different focuses, according to embodiments of the present invention.
Figure 6B:
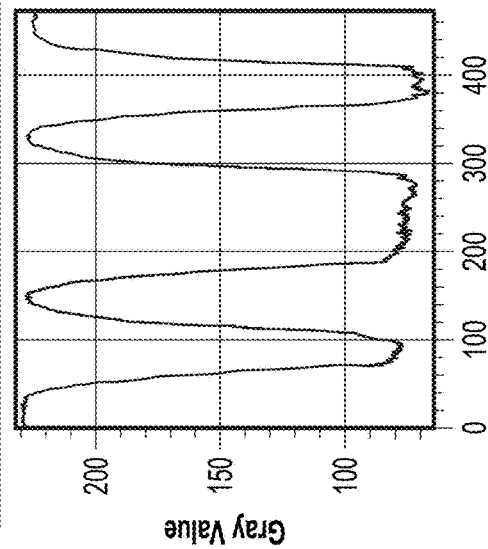
Figure 6A:
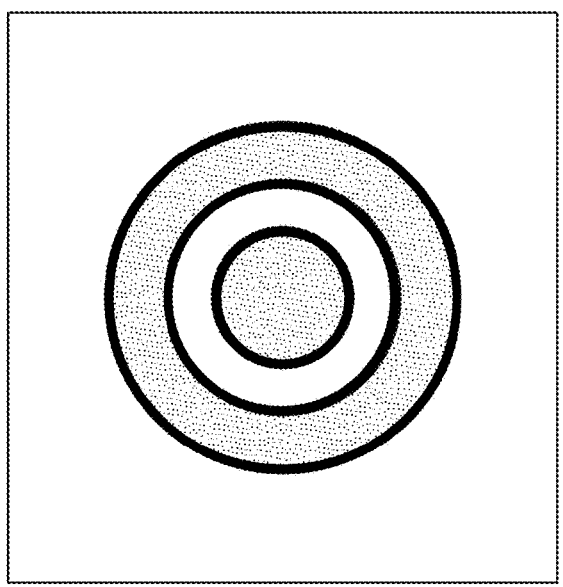
Figure 6A:
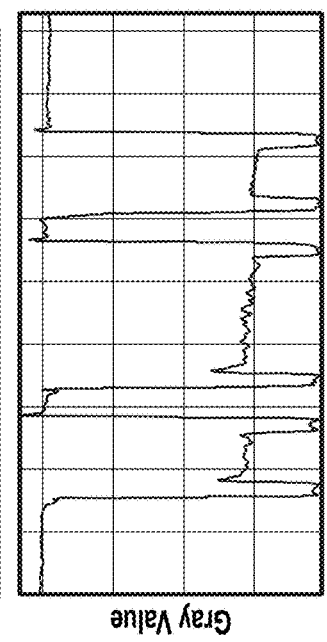

The arrangements in FIGS. 5B and 5C can be used to gauge the focus of the camera. The processing software can determine the brightness or intensity of the white band surrounding the gray center (in FIGS. 5B and 5C) and the brightness or intensity of the gray band surrounding the white band in FIG. 5C. If the focus is good, there will be sharp cutoffs at the transitions between gray and white; if the focus is not good, the cutoffs will be more rounded. Different focuses from colored indicator 531 shown in FIG. 5C are shown in FIGS. 6A-6B. In FIG. 6A, the colored indicator is in focus, and there are sharp cutoffs at the transitions, as shown in the line graph below the colored indicator. In FIG. 6B, the colored indicator is not in focus, and there are more rounded cutoffs at the transitions, as shown in the line graph below that colored indicator. Image blur is similar to the focus problem demonstrated in FIG. 6B, that may result in more rounded cutoffs. If the focus or blur is too great, then the distortion of the image is too great, and distortion determiner 60 would indicate to the user to take another image that is less distorted.

The results illustrated above address some of the shortcomings stated above of the prior methods of determining the effectiveness of a skin treatment. The invention helps normalize the color and size of the skin feature, and thus neutralizes differences in color, lighting, magnification, angle, and distance between the camera and the skin feature. The colored indicator is easy to produce and measure. And using standard, commercial software allows the results to be less prone to variations that may occur if proprietary software were to be used.

Figure 7A:
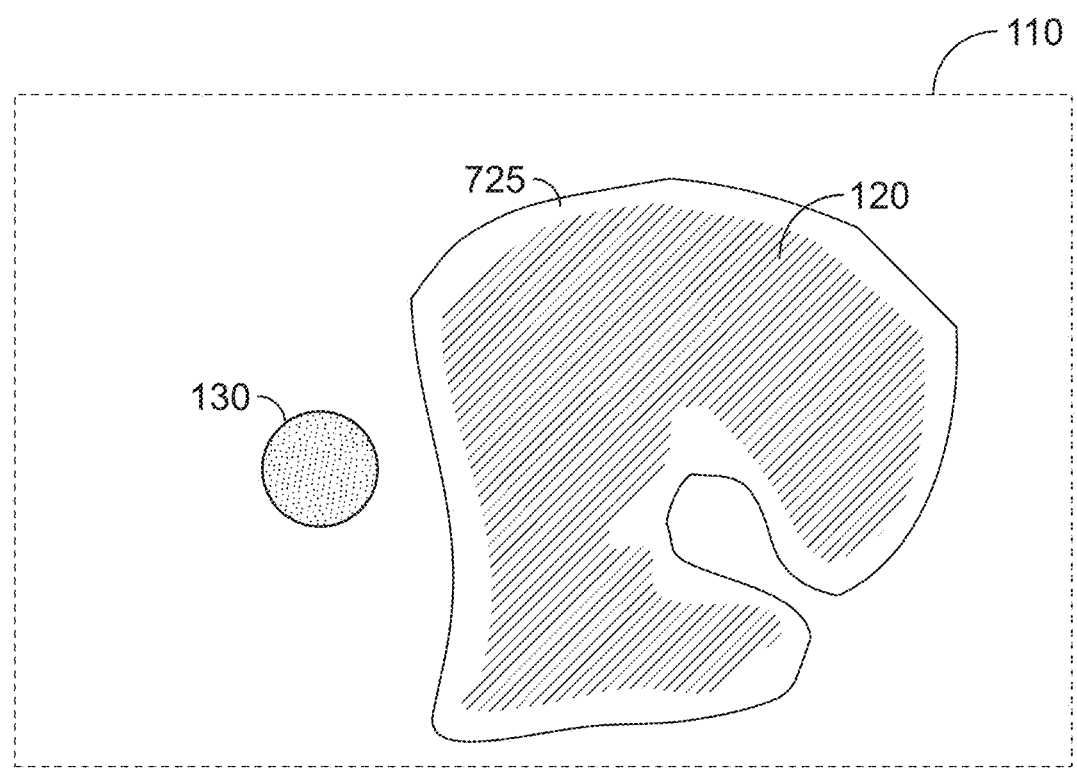
FIG. 7A is a schematic diagram showing a skin feature, the area around the skin feature, and an indicator used to correct color in an image and determine effective starting treatment dose, according to an embodiment of the present invention.
Figure 7B:
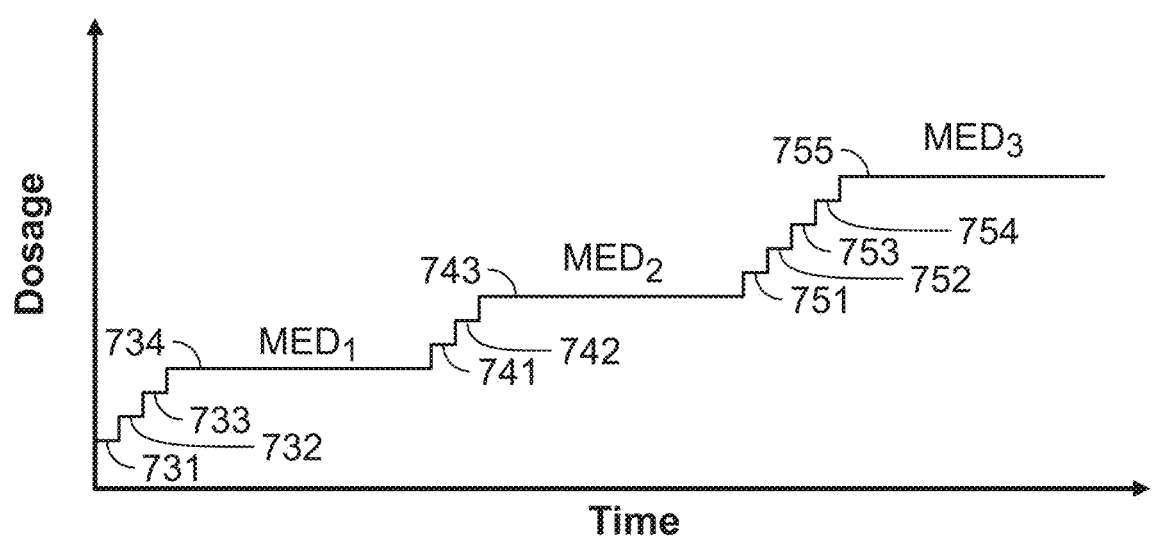
FIG. 7B is graph of dosage vs. time used to determine effective starting and later treatment doses, according to an embodiment of the present invention.

Another embodiment of the invention may be used to determine the Minimal Erythema Dose (MED) or effective starting skin treatment dose. Reference is now made to FIGS. 7A and 7B. FIG. 7A is a schematic diagram showing skin feature 120, the area 725 around the skin feature, and a colored indicator 130. FIG. 7B is a graph of dosage vs. time. As described earlier, patients may use before and after images to determine when a treatment dose begins to elicit a skin reaction, such as by making the skin redder. Such a dose is considered as a starting dose for further treatments. More specifically, in this embodiment a patient may take a first image (e.g., a baseline image) of area 725 around skin feature 120 and colored indicator 130 adjacent to area 725 and skin feature 120, where indicator 130 has a standard color. As described above, the color of the first or baseline image is corrected based on the standard color. The patient then applies a first dose, e.g., 200 mJ/cm², of the skin treatment to skin area 725. This first dose is shown as dosage 731 in FIG. 7B. After a day or two, the patient takes a second image of skin area 725 and the adjacent colored indicator, and the color of the second image is corrected based on the standard color. The system then compares the corrected color of skin area 725 in the first image to the corrected color of skin area 725 in the second image. If the corrected color of skin area 725 in the second image is redder than the corrected color of skin area 725 in the first image, the amount of the first dose, dosage 731, is identified as the effective starting dose or MED.

But if the corrected color of skin area 725 in the second image is not redder than the corrected color of skin area 725 in the first image, the patient increases the dosage of the skin treatment to dosage 732. After waiting another day or two, the patient takes another image of skin area 725 and the adjacent colored indicator. The color of this image is then corrected, and the corrected color of skin area 725 is then compared to the corrected color of skin area 725 in the previous image. If the corrected color of skin area 725 in the later image is redder than the corrected color of skin area 725 in the previous image, then the amount of the current dose, dosage 732, is identified as the effective starting dose.

If the corrected color of skin area 725 in the later image is not redder than the corrected color of skin area 725 in the previous image, the patient increases the dosage of the skin treatment to dosage 733, waits a day or two, and takes another image of skin area 725 and the adjacent colored indicator. This process of increase dosage, wait a day or two, take image of skin area 725, correct color of image, and compare latest image to previous image continues until skin redness begins to appear, at which time the dosage that causes the redness becomes the effective starting dose or MED.

This process is illustrated in FIG. 7B, which is a graph of dosage vs. time, according to an embodiment of the present invention. As described above, the dosage was started at dosage 731, wait one or two days, and then determine if there is redness. Since there was no redness, the dosage was increased to dosage 732 (wait one to two days and compare) and then to dosage 733 (wait one to two days and compare), with no redness appearing. The dosage was then increased to dosage 734, and after one to two days, redness appeared. This dosage, 734, becomes the MED (or $MED_1$ as in FIG. 7B).

$MED_1$ is maintained for some time (typically several weeks), and hopefully there is improvement in the appearance of the skin feature. Then the healthcare provider may suggest increasing the dosage so as to keep improving the condition of the skin feature. So, the patient tries a higher dose, e.g., dosage 741. After one or two days, the patient uses the invention to take another image of skin area 725 and the adjacent colored indicator, and then determines if there is redness. If no redness, the dosage is increased to dosage 742 (wait one to two days and compare) with no redness appearing. The dosage is then increased to dosage 743, and after one to two days, redness appears, then this dosage, 743, becomes the second MED (or $MED_2$ as in FIG. 7B).

$MED_2$ is maintained for some time (typically several weeks), and hopefully there is more improvement in the appearance of the skin feature. The healthcare provider may again suggest increasing the dosage so as to keep improving the condition of the skin feature. So, the patient tries a higher dose, e.g., dosage 751. After one or two days, the patient uses the invention to take another image of skin area 725 and the adjacent colored indicator, and then determines if there is redness. If no redness occurs, the dosage is increased to dosage 752, wait one to two days, and the image is compared to the previous image. If no redness occurs, the dosage is increased to dosage 753, wait one to two days, and the image is compared to the previous image. If no redness occurs, the dosage is increased to dosage 754, wait one to two days, and the image is compared to the previous image. There is still no redness. The dosage is then increased to dosage 755, and after one to two days, redness appears, then this dosage, 755, becomes the third MED (or MEDS as in FIG. 7B).

This process of using the invention to determine the MED in the first place and then to increase the MED over time provides a more objective way to determine redness of the skin.

The treatment in this embodiment is described as light (or UV, UV-B, or narrowband UV-B radiation) therapy, but the treatment may also use thermal or medicinal therapy (e.g., drugs, creams, etc.). The starting dose for thermal therapy may comprise a specific temperature and follow a similar methodology as described above for light therapy. The starting dose for medicinal therapy may comprise a specific strength drug or cream and follow a similar methodology as described above for light therapy.

In sum, the invention allows a patient receiving skin treatments or a healthcare provider providing such treatments objective information regarding the improvement or deterioration in the skin condition due to the treatments. The information can be used to evaluate the effectiveness of different treatments or therapies and also to evaluate the rate and time of lesion improvement. In the case of ultraviolet treatment, the invention may also be used to identify areas outside of the skin feature that may be damaged by the UV radiation. And the invention may be used to determine initial effective starting dose, and to determine increases in dosage during the course of treatment.

Although this invention is described in the context of evaluating the effectiveness of a skin treatment, the techniques described may be used to determine the change in size and color of features other than skin features on a variety of surfaces.

Aspects of the present invention may be embodied in the form of a system, a computer program product, or a method. Similarly, aspects of the present invention may be embodied as hardware, software, or a combination of both. Aspects of the present invention may be embodied as a computer program product saved on one or more computer-readable media in the form of computer-readable program code embodied thereon.

The computer-readable medium may be a computer-readable storage medium. A computer-readable storage medium may be, for example, an electronic, optical, magnetic, electromagnetic, infrared, or semiconductor system, apparatus, or device, or any combination thereof.

Computer program code in embodiments of the present invention may be written in any suitable programming language. The program code may execute on a single computer, or on a plurality of computers. The computer may include a processing unit in communication with a computer-usable medium, where the computer-usable medium contains a set of instructions, and where the processing unit is designed to carry out the set of instructions.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The invention claimed is:

1. A method for evaluating the effectiveness of a skin treatment on a skin feature of a patient, comprising:
   receiving a first image comprising the skin feature and an indicator adjacent to the skin feature, the indicator having a standard color and a known size;
   correcting the color of the first image based on the standard color;
   determining the size of the skin feature in the first image based on the known size;
   receiving a second image generated after the skin treatment is applied, the second image comprising the skin feature and the indicator adjacent to the skin feature;
   correcting the color of the second image based on the standard color;
   determining the size of the skin feature in the second image based on the known size;
   comparing the corrected color of the skin feature in the first image to the corrected color of the skin feature in the second image;
   comparing the size of the skin feature in the first image to the size of the skin feature in the second image; and
   determining the distortion of the first image, the second image, or both images,
   wherein determining the distortion of an image comprises calculating the circularity of the indicator in the image.

2. The method of claim 1, wherein determining the distortion of an image comprises determining the amount of blur in the image.

3. The method of claim 2, wherein determining the distortion of an image comprises determining how unfocused the indicator is by measuring the transition cutoffs of the indicator.

4. The method of claim 1, further comprising storing the color and size information of the first and second images.

5. The method of claim 1, wherein the skin treatment comprises ultraviolet radiation.

6. The method of claim 1, wherein the skin treatment comprises ultraviolet-B radiation.

7. The method of claim 1, wherein the skin treatment comprises narrowband ultraviolet-B radiation.

8. The method of claim 1, wherein the skin treatment comprises medicinal therapy.

9. The method of claim 8, wherein the medicinal therapy comprises a cream or lotion.

10. The method of claim 8, wherein the medicinal therapy comprises an oral medication.

11. A method for determining an effective starting dose of a skin treatment for a skin feature of a patient, comprising:
receiving a first image comprising a skin area outside of the skin feature and an indicator adjacent to the skin area, the indicator having a standard color;
correcting the color of the first image based on the standard color;
receiving a second image generated after a first dose of the skin treatment is applied to the skin area, the second image comprising the skin area and the indicator adjacent to the skin area;
correcting the color of the second image based on the standard color;
comparing the corrected color of the skin area in the first image to the corrected color of the skin area in the second image;
if the corrected color of the skin area in the second image is redder than the corrected color of the skin area in the first image, identifying the amount of the first dose as the effective starting dose;
if the corrected color of the skin area in the second image is not redder than the corrected color of the skin area in the first image, directing the patient to increase the dosage of the skin treatment;
(i) receiving a third image of the indicator and skin area after the increased dose of the skin treatment is applied to the skin area;
(ii) correcting the color of the third image based on the standard color;
(iii) comparing the corrected color of the skin area in the third image to the corrected color of the skin area in the second image;
(iv) if the corrected color of the skin area in the third image is redder than the corrected color of the skin area in the second image, identifying the amount of the increased dose as the effective starting dose;
(v) if the corrected color of the skin area in the third image is not redder than the corrected color of the skin area in the second image, directing the patient to further increase the dosage of the skin treatment;
repeating actions (i)-(v) until the corrected color of the skin area in a further image is redder than the corrected color of the skin area in the preceding image; and
identifying the amount of the last dose as the effective starting dose.

12. The method of claim 11, wherein the skin treatment comprises narrowband ultraviolet-B radiation.

13. The method of claim 11, wherein the skin treatment comprises a cream or lotion.

14. The method of claim 11, wherein the skin treatment comprises thermal therapy.

15. The method of claim 11, further comprising:
maintaining the effective starting dose for a period of time longer than a week;
receiving a maintenance image generated at the end of the period of time, the maintenance image comprising the skin area and the indicator adjacent to the skin area
correcting the color of the maintenance image based on the standard color;
directing the patient to increase the dosage of the skin treatment;
repeating actions (i)-(v) until the corrected color of the skin area in a further image is redder than the corrected color of the skin area in the preceding image; and
identifying the amount of the last dose as an effective later dose.

16. A method for evaluating the effectiveness of a skin treatment on a skin feature of a patient, comprising:
receiving a first image comprising the skin feature and an indicator adjacent to the skin feature, the indicator having a standard color and a known size;
correcting the color of the first image based on the standard color;
determining the size of the skin feature in the first image based on the known size;
receiving a second image generated after the skin treatment is applied, the second image comprising the skin feature and the indicator adjacent to the skin feature;
correcting the color of the second image based on the standard color;
determining the size of the skin feature in the second image based on the known size;
comparing the corrected color of the skin feature in the first image to the corrected color of the skin feature in the second image;
comparing the size of the skin feature in the first image to the size of the skin feature in the second image; and
determining the distortion of the first image, the second image, or both images,
wherein determining the distortion of an image comprises determining the amount of blur in the image and determining how unfocused the indicator is by measuring the transition cutoffs of the indicator.

\* \* \* \* \*